US00PP14691P29

(12) United States Plant Patent
Kearley et al.

(10) Patent No.: US PP14,691 P2
(45) Date of Patent: Apr. 13, 2004

(54) LANTANA PLANT NAMED 'RED SPREAD'

(50) Latin Name: *Lantana camara*
Varietal Denomination: Red Spread

(75) Inventors: Mary E. Kearley, Hawthorne, FL (US); Richard C. Kearley, Jr., Hawthorne, FL (US)

(73) Assignee: Robrick Nursery, Inc., Hawthorne, FL (US)

( * ) Notice: Subject to any disclaimer, the term of this patent is extended or adjusted under 35 U.S.C. 154(b) by 2 days.

(21) Appl. No.: 10/408,185

(22) Filed: Apr. 6, 2003

(51) Int. Cl.[7] ..... A01H 5/00
(52) U.S. Cl. ..... Plt./227
(58) Field of Search ..... Plt./227

*Primary Examiner*—Kent Bell
(74) *Attorney, Agent, or Firm*—C. A. Whealy

(57) ABSTRACT

A distinct cultivar of Lantana plant named 'Red Spread', characterized by its compact, upright and outwardly spreading plant habit; freely flowering habit; inflorescences with red and orange red-colored flowers; and low seed yield.

2 Drawing Sheets

Botanical classification/cultivar designation: *Lantana camara* cultivar Red Spread.

BACKGROUND OF THE INVENTION

The present Invention relates to a new and distinct cultivar of Lantana plant, botanically known as *Lantana camara*, and hereinafter referred to by the cultivar name Red Spread.

The new Lantana is a product of a planned breeding program conducted by the Inventors in Hawthorne, Fla. The objective of the breeding program is to create compact Lantanas with red-colored flowers.

The new Lantana originated from a cross made by the Inventors in August, 2000 of the Lantana cultivar Radiation, not patented, as the female, or seed parent, with an unidentified Lantana selection as the male, or pollen parent. The new Lantana was selected as a single plant from the resulting progeny by the Inventors in a controlled environment in Hawthorne, Fla., on Jun. 30, 2001, on the basis of its growth habit and attractive flower coloration.

Asexual reproduction of the new cultivar by terminal cuttings taken in a controlled environment in Hawthorne, Fla., since Jun. 30, 2001, has shown that the unique features of this new Lantana are stable and reproduced true to type in successive generations.

SUMMARY OF THE INVENTION

Plants of the cultivar Red Spread have not been observed under all possible environmental conditions. The phenotype may vary somewhat with variations in environment and culture such as temperature and light intensity, without however, any variance in genotype.

The following traits have been repeatedly observed and are determined to be the unique characteristics of 'Red Spread'. These characteristics in combination distinguish 'Red Spread' as a new and distinct Lantana cultivar:

1. Compact, upright and outwardly spreading plant habit.
2. Freely flowering habit.
3. Inflorescences with red and orange red-colored flowers.
4. Low seed yield.

Plants of the new Lantana can be compared to plants of the female parent, the cultivar Radiation. In side-by-side comparisons conducted in Hawthorne, Fla., plants of the new Lantana differed from plants of the cultivar Radiation in the following characteristics:

1. Plants of the new Lantana were more compact than and not as upright as plants of the cultivar Radiation.
2. Leaves of plants of the new Lantana were shorter and narrower than leaves of plants of the cultivar Radiation.
3. Plants of the new Lantana had red and orange red-colored flowers whereas plants of the cultivar Radiation had orange and orange red-colored flowers.
4. Plants of the new Lantana produced fewer fruits and seeds than plants of the cultivar Radiation.

Plants of the new Lantana differ from plants of the male parent, the unidentified Lantana selection, primarily in the new Lantana's unique combination of flower coloration, and freely-flowering habit.

Plants of the new Lantana can be compared to plants of the cultivar Spreading Sunset, not patented. In side-by-side comparisons conducted in Hawthorne, Fla., plants of the new Lantana differed from plants of the cultivar Spreading Sunset in the following characteristics:

1. Plants of the new Lantana were more compact than plants of the cultivar Spreading Sunset.
2. Leaves of plants of the new Lantana were longer than leaves of plants of the cultivar Spreading Sunset.
3. Plants of the new Lantana had red and orange red-colored flowers whereas plants of the cultivar Spreading Sunset had orange and yellow orange-colored flowers.
4. Plants of the new Lantana produced fewer fruits and seeds than plants of the cultivar Spreading Sunset.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Lantana.

The photograph on the first sheet comprises a side perspective view of a typical flowering plant of 'Red Spread' grown in a container.

The photograph on the second sheet comprises a close-up view of typical inflorescences and leaves of 'Red Spread'.

DETAILED BOTANICAL DESCRIPTION

In the following description, color references are made to The Royal Horticultural Society Colour Chart, 1995 Edition, except where general terms of ordinary dictionary significance are used. Plants used for the photographs and description were planted in two-gallon containers after rooting and grown for about three months during the spring in a polyethylene-covered greenhouse in Hawthorne, Fla. During the production of the plants in the greenhouse, day temperatures ranged from 18 to 38° C. and night temperatures ranged from 8 to 20° C.

Botanical classification: *Lantana camara* cultivar Red Spread.

Parentage:

*Female parent.*—*Lantana camara* cultivar Radiation, not patented.

*Male parent.*—Unidentified *Lantana camara* selection, not patented.

Propagation:

*Type cutting.*—Terminal cuttings.

*Time to initiate roots, summer.*—About 10 days at 30° C.

*Time to initiate roots, winter.*—About 14 days at 24° C.

*Time to develop roots, summer.*—About 28 days at 30° C.

*Time to develop roots, winter.*—About 35 days at 24° C.

*Root description.*—Fibrous; initially white in color then becoming closer to 156B with development.

*Rooting habit.*—Freely branching; dense.

Plant description:

*Form.*—Flowering subshrub; compact, upright and outwardly spreading; mounded. Freely branching; typically about two lateral branches potentially forming at every node; pinching enhances lateral branch development.

*Plant height.*—About 50 cm.

*Plant diameter.*—About 100 cm.

*Vigor.*—Vigorous, rapid growth rate.

*Lateral branches.*—Length: About 35 cm. Diameter: About 1.8 to 2.2 mm. Internode length: About 6 to 8 cm. Strength: Strong, but flexible. Texture: Rough, coarse pubescence. Color: 144B.

*Foliage description.*—Leaves simple, generally symmetrical and long-persisting; opposite. Length: About 5 to 6 cm. Width: About 2.5 to 3.8 cm. Shape: Lanceolate. Apex: Acute. Base: Attenuate. Margin: Serrate to serrulate with ciliation. Texture, both surfaces: Leathery, rough, coarse; pubescent. Venation pattern: Pinnate, arcuate. Color: Developing and fully expanded foliage, upper surface: 135B. Developing and fully expanded foliage, lower surface: 137C. Venation, upper surface: 135C. Venation, lower surface: 138B. Petiole length: About 3.3 cm. Petiole diameter: About 2 mm. Petiole texture, both surfaces: Pubescent. Petiole color, upper and lower surfaces: 138B.

Flower description:

*Flower type and habit.*—Small salverform flowers arranged in axillary umbels; flowers face mostly upward or outward. Flowers self-cleaning. Very freely flowering with potentially two inflorescences per node; typically about 20 to 30 flowers per umbel.

*Natural flowering season.*—Spring until frost in the autumn; flowering continuous during the flowering period.

*Flower longevity on the plant.*—About one week.

*Fragrance.*—Faint; pleasant.

*Inflorescence diameter.*—About 3.3 cm.

*Inflorescence height.*—About 2 cm.

*Flowers.*—Appearance: Flared trumpet, corolla fused, three to five-parted; flowers roughly rectangular in shape. Diameter: About 1 cm. Corolla tube length: About 1 cm.

*Flower buds.*—Length: About 4 mm. Diameter: About 5 mm. Shape: Roughly spherical. Color: 46A.

*Corolla.*—Arrangement/appearance: Single whorl of three to five petals, fused into flared trumpet. Petal length from throat: About 5 mm. Petal width: About 4 mm. Petal shape: Orbicular. Petal apex: Obtuse, blunt. Petal margin: Entire. Petal lobe texture, upper and lower surfaces: Smooth, velvety. Corolla throat and tube texture: Pubescent. Color: Petals, when opening, upper surface: 40A. Petals, when opening, lower surface: 40C. Petals, fully opened, upper surface: 44A. Petals, fully opened, lower surface: 44C.

*Calyx.*—Arrangement/appearance: One single calyx tube per flower. Sepal length: About 9 mm. Sepal width: About 2.5 mm. Apex: Acute. Texture, upper and lower surfaces: Pubescent. Color, upper and lower surfaces: 137D.

*Peduncles.*—Length: About 6.8 cm. Diameter: About 1.5 mm. Angle: Upright. Strength: Flexible, but strong. Texture: Pubescent. Color: 144A.

*Pedicels.*—Length: Less than 1 mm. Diameter: Less than 1 mm. Angle: Upright. Strength: Flexible, but strong. Texture: Pubescent. Color: Close to 144A.

*Reproductive organs.*—Stamens: Quantity/arrangement: Four per flower, adnate to floral tube. Filament color: White, close to 155D. Anther shape: Ovoid. Anther length: Less than 1 mm. Pistils: Quantity: One per flower. Stigma shape: Globular. Fruit: Amount produced: Scarce. Diameter: About 5 mm. Shape: Roughly spherical. Texture: Smooth. Color: 103A. Seed: Amount produced: Scarce. Diameter: About 2.5 mm. Color: 200D.

Disease/pest resistance: Plants of the new Lantana have not been observed to be resistant to pathogens and pests common to Lantana.

Weather tolerance: Plants of the new Lantana have been observed to be very tolerant to rain and wind.

Temperature tolerance: Plants of the new Lantana have been observed to be tolerant to temperatures ranging from 0 to 38° C.

It is claimed:

1. A new and distinct cultivar of Lantana plant named 'Red Spread', as illustrated and described.

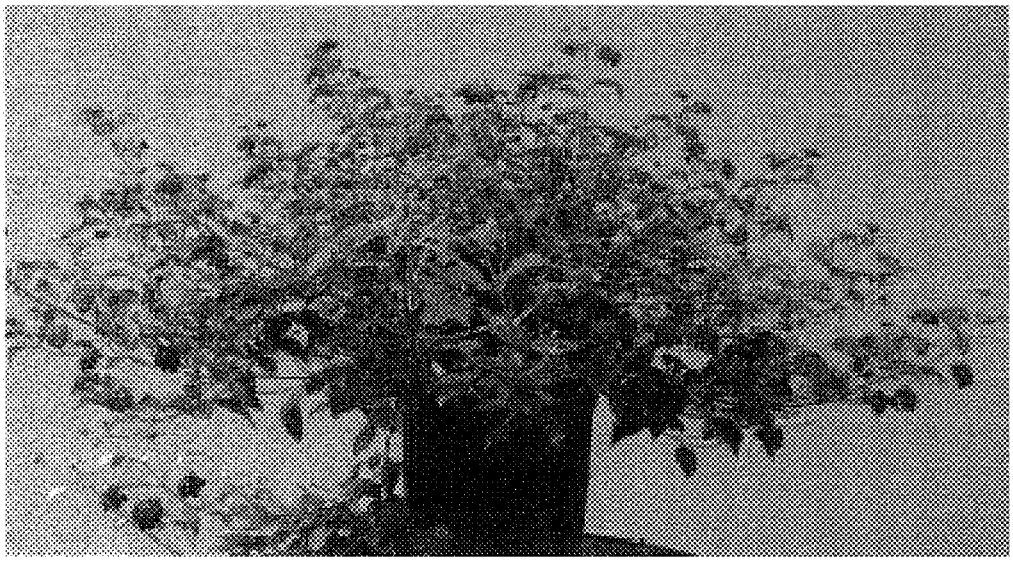

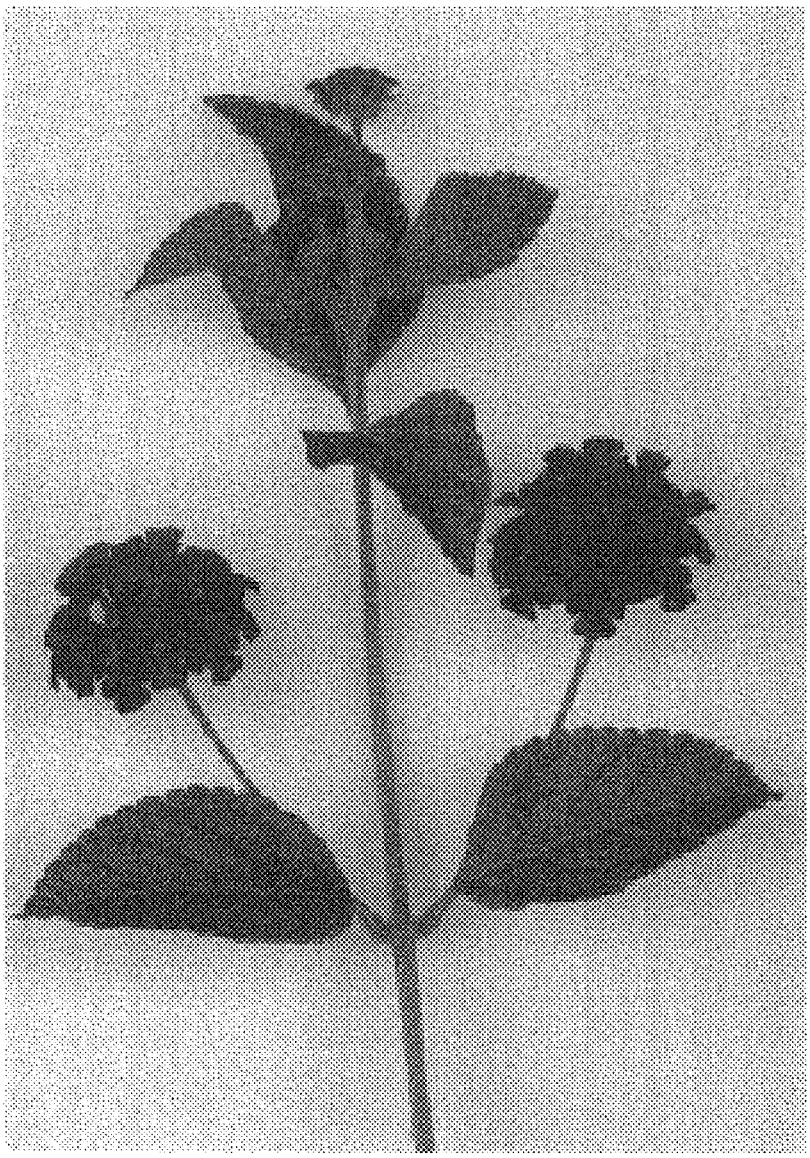

* * * * *